United States Patent [19]

Bhatt et al.

[11] Patent Number: 6,113,881
[45] Date of Patent: *Sep. 5, 2000

[54] HAIR STYLING MOUSSE COMPOSITIONS COMPRISING CARBOXYLATED POLYURETHANE RESINS

[75] Inventors: Darshna Bhatt, Schaumburg; Ramiro Galleguillos, Glendale Heights, both of Ill.

[73] Assignee: Helene Curtis, Inc., Chicago, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/717,428

[22] Filed: Sep. 20, 1996

[51] Int. Cl.⁷ ...................................................... A61K 9/12
[52] U.S. Cl. ............................. 424/45; 424/47; 424/70.11
[58] Field of Search ........................ 424/45, 47, DIG. 1, 424/DIG. 2, 70.11, 78.17, 78.37; 132/202

[56] References Cited

U.S. PATENT DOCUMENTS

| | | |
|---|---|---|
| 3,975,350 | 8/1976 | Hudgin et al. . |
| 4,156,066 | 5/1979 | Gould . |
| 4,359,558 | 11/1982 | Gould et al. . |
| 4,408,023 | 10/1983 | Gould et al. . |
| 4,424,305 | 1/1984 | Gould et al. . |
| 4,439,583 | 3/1984 | Gould et al. . |
| 4,439,585 | 3/1984 | Gould et al. . |
| 4,445,521 | 5/1984 | Grollier et al. . |
| 4,496,535 | 1/1985 | Gould et al. . |
| 4,729,914 | 3/1988 | Kliment et al. . |
| 4,743,673 | 5/1988 | Johnston et al. . |
| 4,780,512 | 10/1988 | Gould et al. . |
| 5,120,816 | 6/1992 | Gould et al. . |
| 5,164,177 | 11/1992 | Bhatt et al. ................................ 424/47 |
| 5,334,691 | 8/1994 | Gould et al. . |
| 5,362,486 | 11/1994 | Nandagiri et al. .................... 424/70.11 |
| 5,639,448 | 6/1997 | Galleguillos et al. ................ 424/70.11 |

FOREIGN PATENT DOCUMENTS

| | | |
|---|---|---|
| 0 619 111 | 10/1994 | European Pat. Off. . |
| 94/03510 | 2/1994 | WIPO . |

*Primary Examiner*—Thurman K. Page
*Assistant Examiner*—R. Bawa
*Attorney, Agent, or Firm*—Matthew Boxer

[57] ABSTRACT

A hair styling mousse composition comprising:
(a) about 0.25% to about 6% by weight of a carboxylated polyurethane resin;
(b) about 0% to about 6% by weight of a second hair fixative resin;
(c) about 0% to about 20% by weight of a lower alcohol; and
(d) about 70% to about 90% by weight water;
wherein the carboxylated polyurethane resin has a weight average molecular weight of 10,000 to about 150,000 is disclosed.

1 Claim, No Drawings

HAIR STYLING MOUSSE COMPOSITIONS COMPRISING CARBOXYLATED POLYURETHANE RESINS

FIELD OF INVENTION

The present invention is directed to hair styling mousse compositions that are applied to the hair to shape, style, and condition the hair. The mousse compositions impart excellent hair styling, detangling, and style retention properties to treated hair, and are washable from treated hair. In particular, the present invention relates to hair styling mousse compositions comprising a carboxylated polyurethane resin, an optional second hair fixative resin, and a carrier comprising water. Preferred mousse compositions are free of foaming surfactants.

BACKGROUND OF THE INVENTION

Normal hair can be so fine, limp, and lacking in body that the hair does not hold a hair set well. Furthermore, hair can lose body and be weakened as a result of being subjected to chemically active hair treatments, such as permanent waves and tints. Additionally, hair can be weakened even further by other contributing factors, such as bleaching by the sun or chlorinated swimming pool water.

The condition and appearance of hair can be improved by applying a composition that conditions the hair and helps maintain the hair in a predetermined configuration, or hairstyle. Hair setting and conditioning can be achieved by applying such a composition to wet hair, fixing the hair by drying, then combing to give finishing touches and provide the desired hairstyle. Similarly, after applying the composition to the hair, the wet hair can be set by using any of a variety of rollers or curlers to mechanically fix the hair in a predetermined configuration before drying. In either case, the wet hair is dried, either by ambient air drying, electric drying, or hot air, i.e., blow, drying, to set the hair.

The inherent problem encountered in hair setting is the natural tendency of hair to return to its natural shape. For example, set hair returns to its natural shape almost immediately if moistened.

Likewise, high humidity conditions accelerate the tendency of hair to return to its natural shape.

Therefore, intensive efforts have been directed toward providing a hair set with sufficient holding power to maintain the desired hairstyle until at least the next shampoo, and, accordingly, giving the hair set a degree of permanency.

As indicated by the natural tendency of hair to return to its natural shape, hair is an elastic structure. As a result, the slight deformations in hair structure resulting from setting the hair are completely reversible. However, the rate of return of hair to its natural shape is dependent upon the method used to deform, or set, the hair. Hair sets performed on wet strands of hair being rolled tightly, either in curls around the finger or on curlers, followed by drying the hair and unrolling the curlers after drying, correspond to the release of hair from a deformation-causing load. The deformation, or set, obtained can last for several days, but the hair set is not retained if the hair is wetted.

Investigators have sought to delay the combined action of natural forces and moisture that cause hair to return to its original state by applying compositions containing naturally occurring or synthetic polymers that assist the hair in retaining the desired hairstyle configuration. When applied to hair from aqueous or aqueous/alcoholic solutions, gels, or mousses, the polymers form a film on the hair, after drying, to help maintain the hair in the desired hair set configuration. The polymeric film promotes cohesion and gives stability to the hair set, and also acts as a moisture barrier. The principal objective of a hair styling composition, therefore, is to cover the styled hair with an invisible polymeric film that gives the styled hair a degree of rigidity, protects the hairstyle against wind and humidity, retains the hairstyle, and imparts a good feel and conditioning to the styled hair.

The general principles of hair styling and setting are thoroughly discussed by C. Zviak, in *The Science of Hair Care*, Marcel Dekker, pp. 149–181 (1986). Zviak reviews both the polymers used in hair styling products and the formulation principles used to produce a hair styling composition that provides such beneficial hair set properties as improved hairstyle retention, easy application and combing, quick drying and nonstickiness, good hair body and bounce, increased hair volume and gloss, and hydrophobicity. It is evident that in the formulation of any end-use hair styling product, some of these benefits must be sacrificed to some degree to achieve a competing benefit. Therefore, the formulation of hair styling compositions has proved difficult.

To overcome some of the inherent disadvantages of the polymers used to set and style hair, and to minimize the drawbacks of a particular polymer used in the formulation, hair styling compositions are available in diversified forms. For example, hair styling compositions are available as plasticizing lotions, plasticizing gels, aerosol mousse foams, all-purpose lotions, hair sprays, holding lotions, conditioners, and shampoos.

One type of hair styling composition is a hair spray product. Hair spray products are applied to wet and/or dry hair and contain a polymer, or polymer mixtures, that remains fixed on the previously styled hair and effects the hair in various ways. For example, a "mechanical" effect is exerted on each individual hair. The film-forming polymers are used to provide a flexible sheath of polymeric film on the shaped hair after drying, and, therefore, for mechanical reasons, retard the return of each individual hair to its natural shape. In addition, the polymeric film provides an overall stiffening of the hair. The hair behaves as if the individual hair strands are welded together, and the final hairstyle has better cohesion, therefore, resisting the natural forces that return the hair to its natural shape. Finally, the polymeric film protects the hair from humidity. The ability of the polymeric film to attract and absorb water preferably is minimal, such that the polymeric film retards moisture uptake by hair and retards the return of the hair to its natural state.

Hair styling gels are another type of hair styling composition. Hair styling gels are applied to wet or damp hair prior to configuring the hair in a predetermined configuration. Hair styling gels are applied by rubbing the gel onto the hair manually. The treated hair then is dried, such as with a blow dryer, and set in a desired configuration.

Another type of hair styling composition is a mousse. A mousse is a liquid composition that typically is applied from an aerosol container. When dispensed from an aerosol container, the mousse forms a foamy material resembling a shaving cream. The mousse is applied to the fingers or the hair, and is manually rubbed into the hair. The foam generated by the mousse is attributed to foaming surfactants present in the composition. As used herein, a "foaming surfactant" is an organic compound having an HLB hydrophilic-lipophilic balance) value of at least about 6, e.g., about 6 to about 25. The foam typically is a fast-breaking foam such that the mousse composition is easily and uniformly rubbed onto damp or dry hair.

In particular, traditional mousse compositions contain a foaming surfactant and are dispensed from an aerosol container onto damp hair or onto dry hair. However, a mousse composition also can be dispensed from a nonaerosol pump spray having a foam actuator. When dispensed from an aerosol container, the dissolved propellant expands and generates a small-bubbled foam. The foam is stable when left undisturbed, but quickly collapses into a liquid when rubbed into the hair. The introduction of air under pressure forms foam when the mousse is applied from a pump spray. To date, all mousse compositions contain a foaming surfactant to generate a foam. The presence of a foaming surfactant, however, can adversely affect the treated hair because the surfactants are hydrophilic, and, therefore, increase the tendency of hair to absorb moisture. In addition, the surfactant can adversely affect the ability of the polymer to form a hard, uniform sheath around hair shafts. In either case, hair set retention is decreased.

Nonionic, cationic, and anionic polymers have been used in hair styling compositions, with the anionic polymers providing the best hair set results. However, anionic polymers also have disadvantages, such as high water solubility, and, therefore, low hydrophobicity; and low substantivity on hair fibers, therefore, generating a crust and flaking due to easy elimination from the hair by combing and brushing. As a result, investigators have continued to search for compounds and compositions that provide the benefits of improved durability and feel of the hair set, while conditioning the hair.

The use of resins, or polymers, in hair styling compositions is well known, as summarized in Grollier et al. U.S. Pat. No. 4,445,521. The resins typically used in hair styling compositions are linear vinyl (e.g., an alkyl vinyl ether) or acrylic (e.g., an alkyl acrylate) polymers prepared by copolymerizing two or more monomers in a free radical polymerization reaction. The vinyl and acrylic-based resins often are used in relatively high concentrations in a hair styling composition to fix the hair in a particular configuration and to provide good hair set retention. However, at high concentrations, the vinyl and acrylic-based resins exhibit disadvantages that adversely affect hair, such as poor combing, poor feel, and excessive stiffness, crust, and flaking.

The vinyl and acrylic-based hair fixative resins conventionally used in hair styling compositions were designed for use in anhydrous alcoholic hair spray compositions. The resins, therefore, had excellent compatibility with, and solubility in, lower alcohols (e.g., ethanol) used in pump spray compositions and hydrocarbons used as propellants in aerosol compositions. However, due to environmental and toxicological concerns, government regulations require a decrease in the amount of organic solvents used in hair setting and related compositions. Therefore, the alcohols and the hydrocarbon gases traditionally present in hair setting compositions, and especially hair sprays, are being replaced with water and water-soluble solvents, like dimethyl ether, that pose less harm to the environment. In addition, the traditional hair sprays are being replaced by hair styling gels and mousses.

The solvent changes required by government regulation made the traditional vinyl and acrylic-based resins unsuitable in aqueous hair setting compositions. The presence of water in hair spray compositions increased the viscosity of the composition, thereby making spraying difficult to impossible when traditional resins were used. The relatively high viscosity of the hair spray compositions, therefore, required a reduction in the resin concentration of the composition, which, in turn, resulted in insufficient hair set retention. The presence of water also increases the tackiness of the resin on the hair, thereby prolonging the drying time of the hair spray on the hair. Water also reduces the hair-wetting ability of the compositions, resulting in beading and flaking of the resin from the hair. In the case of aerosol hair spray products, the combination of water, resin, and propellant gas results in poor delivery of the composition, large aerosol particle size, and beading of the resin. Similar disadvantages were observed when a traditional hair fixative resin was used in an aqueous hair styling gel or mousse.

The disadvantages attributed to traditional vinyl and acrylic resins led investigators to search for new hair fixative resins that overcome the disadvantages associated with the vinyl and acrylic resins. As set forth in European Patent Application 0 619 111, one class of resins is the polyurethanes. However, the hair fixative compositions disclosed in EP 0 619 111 require a base to neutralize, and solubilize, the polyurethane resin. It would be desirable to provide an aqueous hair styling mousse composition that overcomes the disadvantages associated with traditional vinyl and acrylic resins, that imparts good hair style and a natural feel to the hair, that retains the hair set, and that conditions the hair.

SUMMARY OF THE INVENTION

The present invention is directed to hair styling mousse compositions containing (a) a hydrophilic, carboxylated polyurethane resin, (b) an optional second hair fixative resin, and (c) a carrier comprising water. Preferably, the mousse compositions are free of foaming surfactants and lower alcohols. The optional second hair fixative resin is a traditional hair setting resin, such as a vinyl or acrylic resin. The optional second hair fixative resin can be an anionic, cationic, or nonionic resin because each class of resin is compatible with the carboxylated polyurethane resin.

The hair styling mousse compositions are applied as a small-bubbled foam, and after rubbing onto the hair, impart a soft, natural feel to treated hair, and provide superior hairstyle retention, even at a high relative humidity. The hair styling mousse compositions also detangle hair and condition the hair. Such results are unexpected because traditional hair setting resins are hydrophobic. In contrast, the carboxylated polyurethane resins are hydrophilic, yet provide a soft, natural feel to the hair, and the hair is not tacky. In addition, it is surprising that a foaming surfactant is not an essential ingredient with respect to generating a foam, either from an aerosol or nonaerosol composition. Furthermore, the carboxylated polyurethane resins are soluble in water, and hydroalcoholic solutions, without the need to neutralize the resin with a base. Therefore, the hair styling mousse compositions contain a low amount of VOC, preferably are free of lower alcohols, and are safe to the environment.

In particular, the present invention is directed to hair styling mousse compositions comprising: (a) about 0.25% to about 6%, by total weight of the composition, of a carboxylated polyurethane resin, (b) 0% to about 6%, by total weight of the total composition, of an optional second hair fixative resin, and (c) a carrier comprising water. The hair styling mousse compositions have a pH of about 6 to about 10. In a preferred embodiment, the weight ratio of the optional second hair fixative resin to the carboxylated polyurethane resin is about 1 or less, i.e., 0 to about 1.

The mousse composition can be applied to the hair as a foam from a pump spray. Alternatively, if an aerosol composition is desired, the composition can further comprise about 5% to about 30%, by total weight of the composition, of a propellant. Optional ingredients also can be incorporated into the mousse composition.

The polyurethane resins, also termed polycarbamyl polyglycols, have pendant carboxyl groups and are hydrophilic. The carboxyl groups can be a carboxylic acid group (i.e., a $CO_2H$ group) an ester group (i.e., a $CO_2R$ group wherein R is an alkyl group containing one to three carbon atoms), or a mixture thereof. The polyurethane resin also can be a copolymer of polyvinylpyrrolidone and a polyurethane, termed a PVP/polycarbamyl polyglycol ester.

The polyurethane resins have good tear strength, excellent washability, good adhesion, and are soluble in water and polar solvents, thereby making them useful in mousse compositions. In addition, the polyurethane resins, alone and in combination with the optional second hair fixative resin, form clear, i.e., transparent, low viscosity solutions in neutral to slightly basic aqueous solvents. Compositions containing the hydrophilic polyurethane resins, therefore, are sprayable. The carboxylated polyurethane resins form elastic films that give treated hair a natural feel.

The hair styling mousse compositions can be designed to impart a natural feel, a soft conditioned feel, or a stiff feel to treated hair by a judicious selection of: (a) the optional second hair fixative resin and (b) the weight ratio of carboxylated polyurethane resin to optional second hair fixative resin.

The mousse compositions have a very low viscosity for excellent delivery properties, and foam on the hair or fingertips during application. After rubbing the mousse through wet or damp hair, followed by thoroughly drying the hair, the polyurethane mousse gels on the hair. The optional second hair fixative resin is included in the composition to impart a desired degree of stiffness to treated hair and to reduce crust and flaking. The hair styling mousse compositions, therefore, impart superior hair set retention and feel to treated hair. Surprisingly, the present mousse compositions generated a consumer-acceptable foam, even in the absence of a foaming surfactant.

In accordance with an important aspect of the present invention, the hair styling mousse compositions exhibit improved washability from the hair when the carboxylated polyurethane resin has an acid value of at least about 7 mg KOH/g (milligrams potassium hydroxide per gram of resin), and preferably about 7 to about 50 mg KOH/g of resin. The polyurethane resins do not require neutralization with a base to provide a useful aqueous mousse composition.

In accordance with one embodiment of the present invention, the carboxylated polyurethane resin used in the hair styling mousse composition is an ester polyurethane resin, such as a copolymer of polyvinylpyrrolidone and a polyurethane. In another embodiment, the carboxylated polyurethane resin is produced by reacting: (a) a diol component comprising a polyoxyalkylene diol; (b) an alkylene glycol; (c) a diisocyanate; (d) water in an amount of about 0.05% to about 0.5% by weight of the mixture; and (e) a 2,2-di(hydroxymethyl)alkanoic acid, preferably 2,2-di (hydroxymethyl)propionic acid, wherein the ratio of NCO (isocyanate) groups to OH (hydroxyl) groups in the water, diol, and glycol, i.e., the R-value, is about 0.5 to about 1.

The hydrophilic, carboxylated polyurethane resin contains polyoxyalkylene units, i.e., soft segments, and/or alkylene units, i.e., hard segments, connected by urethane linkages. Preferably, the carboxylated polyurethane resin contains soft and hard segments. Also incorporated into the polymer chain is a small amount of diol having a pendant carboxyl group. The polymer chain also contains urea linkages resulting from a reaction between the water and isocyanate groups, which modify the hair styling properties of the polyurethane.

Polyoxyethylene soft segments of the polyurethane resin impart hydrophilicity to the polyurethane. Soft segments derived from polyoxypropylene and polyoxytetramethylene diols provide a softer, but less hydrophilic, polyurethane. Hydrophilic polyurethane resins having improved strength and superior adhesive properties can be formed by using combinations of polyoxyalkylene diols.

In another embodiment of the present invention, the carboxylated polyurethane resins used in the hair styling mousse composition are produced from (a) a major portion of polyoxyethylene diol having a number average molecular weight ($M_n$) of 6000 to 10,000; (b) an alkylene glycol, preferably diethylene glycol, cyclohexanedimethanol, or dipropylene glycol; (c) a diisocyanate; (d) water in the amount of about 0.05% to about 0.5% by weight; and (e) a 2,2-di -(hydroxymethyl)alkanoic acid, wherein the ratio of NCO to OH in the water, diol, and glycol mixture (i.e., the R-value) is about 0.5 to about 0.98. These polyurethane resins are soluble in dilute (neutral to basic) aqueous solutions, and exhibit good sprayability, superior feel, low flaking, desirable crust, and good set retention when applied to hair. The polyurethane resins are hydrophilic, and provide a soft feel in a hydrated state. In a particular embodiment of a polyurethane resin produced with a major portion of polyoxyethylene diol, water is added in the amount of about 0.1% to about 0.45% by weight, and the ratio of NCO to OH of the water, diol and glycol mixture (i.e., the R-value) is about 0.6 to about 0.98 to provide a carboxylated polyurethane resin having improved adhesiveness to the hair, and improved slip, i.e., good combing properties. Another aspect of the present invention is to provide a hair styling mousse composition that provides good hair set retention at high relative humidity and that imparts a natural feel to the hair. Accordingly, a hydrophilic polyurethane resin incorporated into a present hair styling mousse composition has a weight average molecular weight ($M_w$) of about about 10,000 to about 150,000, preferably 15,000 to about 100,000, and to achieve the full advantages of the present invention about 15,000 to about 75,000. The polyurethane resins also have a polydispersibility index (PDI) of about 1 to about 4, and preferably about 1 to about 3. Preferred polyurethane resins have an R-value of about 0.65 to about 0.85.

In accordance with another important aspect of the present invention, the carboxylated polyurethane resin modifies the properties of the optional second hair setting resin to provide a low viscosity mousse composition that can be easily applied to the hair and gives hair a natural through a stiff feel, as desired, while imparting good set retention without crust or flaking. In addition, the hair styling mousse compositions preferably are free of a foaming surfactant because the carboxylated polyurethane resin has an ability to generate a consumer-acceptable foam, and are free of a lower alcohol.

DETAILED DESCRIPTION OF THE INVENTION

The present hair styling mousse compositions are sprayable hair styling aids containing a carboxylated polyurethane resin and an optional second hair setting resin, and preferably are free of: (a) a foaming surfactant and (b) of a lower alcohol. The polyurethane resins are soluble in water and a broad range of water/alcohol mixtures, and help solubilize the optional second hair setting resin, thereby permitting the preparation of aerosol and nonaerosol, i.e., pump spray, compositions containing a low amount of volatile organic compounds (VOC), and in some cases compositions free of VOC. The hair styling mousse compositions also can contain propellant gases for application as an aerosol spray.

The carboxylated polyurethane resins possess thermal properties that allow styling of the hair with curling irons or blow dryers, and foaming properties that allow omission of a foaming surfactant from the mousse composition. The present hair styling mousse compositions, therefore, overcome problems and disadvantages associated with compositions which contain only a traditional acrylic or vinyl-based hair fixative resin, and provide improved styling, hair set retention, hair feel, washability, and spray properties.

In particular, the present hair styling mousse compositions comprise about 0.25% to about 6%, and preferably about 0.5% to about 5%, by total weight, of a carboxylated polyurethane resin. To achieve the full advantage of the present invention, the compositions comprise about 1% to about 5%, by weight of the composition, of a carboxylated polyurethane resin.

The polyurethane resins are linear, hydroxyl-terminated copolymers having pendant carboxyl groups. The hydrophilic polyurethanes typically are ethoxylated and/or propoxylated at least at one terminal end. The carboxyl group can be a carboxylic acid group or an ester group wherein the alkyl moiety of the ester group contains one to three carbon atoms. The carboxylated polyurethane resin also can be a copolymer of polyvinylpyrrolidone and a polyurethane, having a CTFA designation PVP/polycarbamyl polyglycol ester. In accordance with an important feature of the present invention, the polyurethane resins can be solubilized in water, or in a hydroalcoholic solution, in the absence of a base.

The carboxylated polyurethane resins are soft and flexible, and have a melting point of about 40° C. to about 120° C., and preferably about 60° C. to about 100° C. To achieve the full advantage of the present invention, the polyurethane resins have a melting point of about 70° C. to about 90° C.

The carboxylated polyurethane resins provide treated hair with a conditioned, soft, nontacky, natural feel, while maintaining good style retention. The carboxylated polyurethane resins also have physical properties which make them suitable for use in hair styling mousse compositions. For example, the carboxylated polyurethane resins are (a) capable of generating a foam, (b) sprayable, (c) soluble in water and hydroalcoholic solutions, (d) propellant tolerant, and (e) fast drying. The polyurethane resins also exhibit good wet combing properties, and are washable from the hair.

The hydrophilic polyurethane resins are prepared using an aliphatic diisocyanate, an aromatic diisocyanate, or a mixture thereof. An aliphatic diisocyanate is preferred. The diisocyanate is typically interacted with a low molecular weight glycol or triol, such as ethylene glycol, diethylene glycol, propylene glycol, glycerol, hexylene glycol, cyclohexanediol, cyclohexanedimethanol, 1,4-butanediol, tripropylene glycol, triethylene glycol, dipropylene glycol, or mixtures thereof, wherein the glycol or triol has at least two hydroxyl groups and a molecular weight up to about 200, to provide a polyurethane. The diisocyanate also can be reacted with a polymeric dihydroxy-terminated oligomer, e.g., a polyoxyalkylene glycol having a molecular weight of about 200 to 20,000 to provide a hydrophilic polyurethane. Exemplary oligomers include, but are not limited to, polypropylene glycols, polyethylene glycols, ethylene glycol-propylene glycol copolymers, polybutylene glycols, and mixtures thereof. Preferably, a diisocyanate is interacted both with a low molecular weight diol or triol and with an oligomer to provide a hydrophilic polyurethane.

Exemplary, but nonlimiting, diisocyanates include trimethylhexamethylene diisocyanate, isophorone diisocyanate, decamethylene-1,10-diisocyanate, cyclohexane-1,2-diisocyanate, methylene bis(cyclohexyl-4-isocyanate), toluene-1,4-diisocyanate, toluene-2,6-diisocyanate, diphenylmethane-4,4'-diisocyanate, 3,3'-dimethyldiphenylmethane-4,4'-diisocyanate, m-phenylene diisocyanate, p-phenylene diisocyanate, chlorophenylene diisocyanate, hexamethylene-1,6- diisocyanate, tetramethylene-1,4-diisocyanate, cyclohexane-1,4-diisocyanate, naphthalene-1,5-diisocyanate, 1-methoxyphenyl-2,4-diisocyanate, 4,4'-biphenylene diisocyanate, 3,3'-dimethoxy-4,4'-biphenyl diisocyanate, 3,3'-dimethyl-4,4'-biphenyl diisocyanate, 3,3'-dichlorophenyl-4,4'-diisocyanate, 2,2',5,5'-tetrachlorodiphenyl-4,4'-diisocyanate, trimethylhexamethylene diisocyanate, m-xylene diisocyanate, and mixtures thereof.

The polyurethane resin contains pendant carboxyl groups to improve the water solubility or dispersibility of the polyurethane resin. Preferably, the number of carboxylic acid groups is sufficient to give the polyurethane resin an acid value of at least about 7, and preferably about 7 to about 50, mg KOH/g resin. Examples of useful carboxylated polyurethanes are disclosed in Gould et al. U.S. Pat. No. 5,000,955, incorporated herein by reference. Other useful hydrophilic polyurethanes are disclosed in U.S. Pat. Nos. 3,822,238; 4,156,066; 4,156,067; 4,255,550; and 4,743,673, also incorporated herein by reference.

A polyurethane resin incorporated into a present hair styling mousse composition preferably comprises a reaction product of a diol component, an alkylene glycol, an aliphatic diisocyanate, water, and a 2,2-di-(hydroxymethyl)alkanoic acid. Alternatively, an amine, such as diglycolamine, can be substituted for at least a portion of the water in the reaction mixture. Aqueous solutions of the hydrophilic carboxylated polyurethane resins have low viscosities, can create a foam, and impart a soft feel, good set retention, reduced flaking and crust, and improved hair setting and conditioning properties to treated hair.

In one embodiment, the polyurethane resin comprises the reaction product of: a diol component comprising a polyoxyalkylene diol, preferably a polyoxyethylene diol having a number average molecular weight ($M_n$) of about 200 to about 20,000, a polyoxypropylene diol having an $M_n$ of about 200 to about 2500, a block copolymer of ethylene oxide and propylene oxide having an $M_n$ of about 1,000 to about 9,000, or a polyoxytetramethylene diol having an $M_n$ of about 200 to about 4,000; about 0.01% to about 10% by weight of a low molecular weight alkylene glycol selected from the group consisting of ethylene glycol, propylene glycol, 2-ethyl-1,3-hexanediol, tripropylene glycol, triethylene glycol, 2,4-pentanediol, 2-methyl-1,3-propanediol, 2-methyl-1,3-pentanediol, cyclohexanediol, cyclohexanedimethanol, dipropylene glycol, diethylene glycol, and mixtures thereof; an organic diisocyanate; a 2,2-di-(hydroxymethyl)alkanoic acid; and water in an amount of about 0.05% to about 0.5% by weight of the reaction mixture, wherein the NCO/OH ratio (i.e., the R-value) is about 0.5 to about 1, and preferably about 0.6 to about 0.98. To achieve the full advantage of the present invention, the R-value is about 0.65 to about 0.85.

An amine can be used in the reaction mixture for at least a portion of the water. The amine can be added to the reaction mixture in an amount of about 0.01% to about 0.8% by weight amine, preferably about 0.02% to about 0.5% amine to about 0.01% to about 0.2% water in the reaction mixture. Amines that can be used in the reaction are ethylenediamine, propylenediamine, monoethanolamine, diglycolamine, and JEFFAMINE D1-230, D-400, D-2000, D-4000, ED-0600, ED-900, or ED-2001. The hydroxylamines and the JEFFAMINE products are manufactured by Texaco Chemical Company. Preferably, the amine is a hydroxylamine, and most preferably the amine is monoethanolamine and/or diglycolamine.

The polyoxyethylene diols are available from Union Carbide Corporation under the trademark CARBOWAX, such as CARBOWAX® 1450 and CARBOWAX® 8000 wherein the number represents number average molecular weight. The polyoxypropylene diols (PPG) are available from various sources, such as the PPG series of ARCO NIAX® PPG 1025, PPG 425, PPG 725, PPG 1225, and PPG 2025, and as R2134 (2200) and R2135 (4400), wherein the number represents number average molecular weight. Triols also are available from ARCO as NIAX® Polyols 11-34, LG-650, LG-56, LG-168, LHT-28, LHT-240. The polyoxytetramethylene diols are available from E.I. DuPont de Nemours as TERATHANE 600, 1000, 1400, 2000, and 2900. Polyetherpolycarbonate is available from BASF under the tradename polytetrahydrofuran 1000 CD and 2000 CD.

A block polyoxyalkylene polymer also can be used in the reaction. For example, a propylene oxide terminated block of ethylene glycol manufactured by BASF under the tradename PLURONIC R and a ethylene oxide terminated block of propylene glycol manufactured by BASF under the tradename of PLURONIC can be used for the polyoxyalkylene in the reaction. Examples of the block copolymers of the sequential addition of ethylene oxide and propylene oxide to ethylene diamine are made by BASF under the tradename of PLURONIC, such as PLURONIC F68, F64, F127, L35, L92, L82, 17R2, and 25R2.

The amount of polyoxyalkylene diol having an $M_n$ of 200 to 20,000 in the polyurethane resin can vary from about 10% to about 90%, preferably about 30% to about 90%, and most preferably about 40% to about 90%, by weight, and the number average molecular weight ($M_n$) of the polyoxyalkylene diol can vary from about 200 to about 20,000, preferably from about 400 to about 12,000, and more preferably from about 800 to about 10,000.

Preferably, the polyoxyalkylene diol used in forming the hydrophilic polyurethane resin is polyoxyethylene diol. The blends of polyoxyalkylene diols contain at least about 10% polyoxyethylene diol, preferably at least about 20% polyoxyethylene diol, and most preferably at least about 25% polyoxyethylene diol, by weight.

The alkylene glycols can be purchased from numerous sources. For example, propylene glycol can be purchased from Aldrich Chemical Company as 1,2-propanediol. The amount of the alkylene glycol (hard segment) component in the polyurethane resin can be about 0.01% to about 20%, preferably about 0.05% to about 15%, more preferably about 0.1% to about 12%, still more preferably about 0.5% to about 10%, and most preferably about 1% to about 8%, by weight of the reaction mixture.

The diisocyanate in the reaction mixture can be an aliphatic diisocyanate, an aromatic diisocyanate, or a mixture thereof. The aliphatic diisocyanates are preferred. An especially preferred diisocyanate is methylene bis(cyclohexyl-4-isocyanate). Other examples of diisocyanates are trimethyl hexamethylene diisocyanate and isophorone diisocyanate. Representative examples of the preferred aliphatic diisocyanates include, but are not limited to tetramethylene diisocyanate, hexamethylene diisocyanate, trimethylene diisocyanate, trimethylhexamethylene diisocyanate, cyclohexyl-1,2-diisocyanate, and cyclohexyl-1,4-diisocyanate. Examples of aromatic diisocyanates include 2,4-toluene diisocyanate and 2,6-toluene diisocyanate. Also suitable are the isocyanate equivalents which form urethane linkages, exemplified by nitrile carbonates, such as adiponitrile carbonate of U.S. Pat. No. 4,810,543, incorporated herein by reference. The amount of diisocyanate varies from about 3% to about 80%, preferably from about 4% to about 70%, more preferably from about 5% to about 60%, still more preferably from about 6% to about 55%, and most preferably from about 6.5% to about 50%, by weight. The polyurethane resins are prepared by reacting the polyoxyalkene diols with the diisocyanates.

The amount of water in the reaction mixture is about 0.05% to about 0.5%, and more preferably about 0.1% to about 0.45%, by weight, of the reaction mixture.

In another embodiment, the hydrophilic polyurethane resin comprises a reaction product of: (a) a diol having a major portion of a polyoxyethylene diol having an $M_n$ of 6,000 to 10,000, and a minor portion of a polypropylene diol having an $M_n$ of about 1,000 to about 3,500 or a polyoxyethylene diol having an $M_n$ of about 200 to about 2000; (b) an alkylene glycol; (c) a diisocyanate; (d) water in an amount of about 0.05% to about 0.5% by weight of the reaction mixture; and (e) a 2,2-di(hydroxymethyl)alkanoic acid, and an equivalent mole weight ratio of NCO to OH of the water, diol and glycol of about 0.5 to about 1. Preferably at least 45% of the polyoxyethylene glycol of $M_n$ about 8000, more preferably at least about 55%, still more preferably at least about 65%, and most preferably at least 75%, by weight, is used in the total reaction mixture. The amount of the lower molecular weight polyoxyethylene diol having an $M_n$ of about 200 to about 2,000 is about 1% to about 15%, and preferably from about 2% to about 10%, by weight, of the reaction mixture. Preferably, the alkylene glycol is diethylene glycol, cyclohexanedimethanol, dipropylene glycol, or a mixture thereof.

The 2,2-di-(hydroxymethyl)alkanoic acid preferably is dimethylolpropionic acid. The amount of dimethylolpropionic acid is about 1% to about 8%, preferably about 1.5% to about 7%, and most preferably about 2% to about 6% by weight of the reaction mixture. Preferably, the final product has an acid value of at least about 7 mg KOH/g resin. To achieve the full advantage of the invention, the polyurethane resin has an acid value of about 7 to about 50 mg KOH/g resin. The sum of all ingredients, including the diols, glycols, water, and diisocyanate in the reaction mixture totals 100% by weight.

An amine can be used in place of a portion of the water in the reaction mixture. An amount of about 0.15% to about 0.6% by weight amine, based on diglycolamine, is used with about 0.06% to about 0.5% of water, more preferably about 0.1% to about 0.4% of water, and most preferably of about 0.15% to about 0.3% of water.

The preferred diol is a polyoxyethylene diol, preferably a polyoxyethylene diol of $M_n$ about 200 to about 5,000. The preferred water level is about 0.1% to about 0.45%, and most preferably about 0.15% to about 0.4%, by weight.

The ratio of NCO to OH groups from the diol, alkylene glycol, amines and water (i.e., the R-value) in the reaction mixture is about 0.5 to about 1, preferably about 0.6 to about 0.98, and most preferably about 0.65 to about 0.85. The weight average molecular weight ($M_w$) of the carboxylated polyurethane resin is about 10,000 to about 150,000, preferably about 15,000 to about 100,000, and most preferably about 15,000 to about 75,000.

The carboxylated polyurethane resins of this embodiment are especially useful in hair styling mousse compositions because the polyurethane resins are soluble in dilute neutral to basic aqueous solutions, and in ethanol/water mixtures, to form low viscosity solutions. Solutions of the polyurethane resins also exhibit improved sprayability, the ability to generate foam in the absence of a foaming surfactant, improved feel of sprayed hair, low flaking and crust, and improved hair set retention. The carboxylated polyurethane resins maintain these advantageous properties when admixed with an optional second hair fixative resin, and improve the properties of the optional second hair fixative resin, e.g., increased water solubility, decreased solution viscosity, improved hair feel, and reduced crust and flaking.

For hair styling mousse compositions, the hydrophilicity of the polyurethane resin is an unexpected important property in combination with other desirable properties, such as washability. Conventional hair fixative resins are hydrophobic materials that impart a stiff feel to treated hair. The polyurethane resins are hydrophilic materials that give hair a soft, natural feel, yet are adhesive to the hair and impart excellent hair set retention. A combination of a conventional hair fixative resin and a polyurethane resin retains the desirable properties of each resin and allows a desired degree of stiffness to be imparted to the hair. It also has been found that the hair styling properties of the polyurethane resin can be effected by small changes in the amount of water, the ratio of NCO/OH, and the amount of the di(hydroxymethyl)alkanoic acid in the reaction mixture.

Further, the weight average molecular weight of the carboxylated polyurethanes can be decreased or increased by modifying the amount of water in the reaction mixture within a predetermined range. The above-described polyurethane resins have an $M_w$ of about 10,000 to about 150,000, and preferably about 15,000 to about 100,000; and a kinematic viscosity at 3 wt. % in 55/42 ethanol/water (by weight) of about 1 to about 40 centistokes (cs), formed from a range of water of about 0.1% to about 0.3% by weight of the reaction mixture, a NCO/OH ratio (i.e., R-value) of about 0.75 to about 0.95, and a range of dimethylolpropionic acid of about 1% to about 2.7% by weight of the reaction mixture. A polyurethane having an $M_w$ of about 55,000 to about 150,000 can be formed using 0.3% to about 0.45% by weight water, a preferred NCO/OH ratio of about 0.75 to about 0.98, and about 1% to about 2.7% by weight dimethylolpropionic acid.

A polyurethane resin having an $M_w$ of less than about 25,000 can be formed using a water level of about 0.25% to about 0.4% by weight of the reaction mixture, a ratio of NCO/OH about 0.60 to about 0.75, and a range of dimethylolpropionic acid of about 3% to about 6.5% by weight of the reaction mixture. The polyurethane resin has a kinematic viscosity at 3 wt. % in a 55/42 ethanol/water solution (by weight) of about 1 to about 10 Cs. These polyurethane resins are useful as hair styling aids and form low viscosity solutions in water and hydroalcoholic solutions.

Polyurethane resins prepared using an amount of water of about 0.1% to about 0.4% by weight in the reaction mixture, and a NCO/OH ratio of about 0.55 to about 0.95, preferably from about 0.6 to about 0.7, impart a set retention at 30 minutes of about 80% to about 90%. An amount of water of about 0.15% to about 0.45% by weight in the reaction mixture and a NCO/OH ratio of about 0.6 to about 0.92, preferably from about 0.7 to about 0.85, can be used to provide polyurethane resins imparting a set retention of about 85% to about 98% at 30 minutes.

Alternatively, small amounts of diglycolamine can be substituted for the water in the reaction mixture, e.g., about 0.02% to about 1%, preferably from about 0.03% to about 0.75%, more preferably from about 0.04% to about 0.5%, and most preferably from 0.05% to about 0.4%, by weight diglycolamine can be used in the reaction mixture.

The alkylene glycol used in this embodiment can be, for example, ethylene glycol, diethylene glycol, propylene glycol, dipropylene glycol, cyclohexanediol, 1,4-butanediol, cyclohexanedimethanol, tripropylene glycol, or triethylene glycol; preferably diethylene glycol, cyclohexanedimethanol, or dipropylene glycol; and most preferably diethylene glycol. The amount of the alkylene glycol (hard segments) in the reaction mixture is about 0.01% to about 20%, preferably about 0.05% to about 15%, more preferably about 0.1% to about 12%, still more preferably about 0.5% to about 10%, and most preferably about 1% to about 5%, by weight.

In each embodiment, the polyurethane-forming reaction is catalyzed by known catalysts. Tin-containing catalysts, such as tin salts or organotin esters, for example, stannous octoate and dibutyltin dilaurate, or tertiary amines, such as triethylene diamine and N,N,N',N'-tetramethyl-1,3-butane diamine, are preferred. The catalyst is used in an amount effective to catalyze the reaction, i.e., about 0.001 to 1 weight percent of the total weight of the reaction mixture. Reaction temperature is about 40° C. to about 120° C.

In the previous embodiments, the carboxylated polyurethane resin contained carboxylic acid groups. However, carboxylated polyurethane resins wherein carboxylic acid groups are converted to ester groups with an alcohol having one to three carbon atoms also can be utilized as the carboxylated polyurethane resin. Other useful carboxylated polyurethane resins are PVP/polycarbamyl polyglycol esters, which are copolymers of polyvinylpyrrolidone and a polyurethane. These carboxylated polyurethane resins are available commercially from Phoenix Chemical, Inc., Somerville, N.J., as PECOGEL A-12, PECOGEL H-12, PECOGEL H-115, and PECOGEL H-1220.

In addition to the carboxylated polyurethane resin, the hair styling mousse composition contains 0% to about 6%, and preferably about 0.25% to about 5%, by weight of an optional second hair fixative resin. To achieve the full advantage of the present invention, the hair styling mousse composition contains about 1% to about 5%, by weight of the composition, of an optional second hair fixative resin. Preferably, the weight ratio of optional second hair fixative resin to carboxylated polyurethane resin in the composition is about one or less, i.e., 0 to about 1. The optional second hair fixative resin can be a nonionic, cationic, or anionic resin, because the carboxylated polyurethane resin is compatible with each class of resins. It also is envisioned that the optional second hair fixative resin is a mixture of two or more hair fixative resins in a total amount of 0% to about 6% by weight of the composition.

The optional second hair fixative resin preferably is a hydrophobic compound that retards the tendency of hair to absorb water. The optional second hair fixative resin also is a hard, brittle compound having a glass transition temperature of about 100° C. or greater, preferably about 110° C. or greater, e.g., up to 200° C. An important feature of the optional second hair fixative resin is to reduce flaking attributed to the carboxylated polyurethane resins, and to impart hair set properties typically associated with the optional second hair fixative resin to the hair.

In particular, the optional second hair fixative resin imparts a desired and predetermined degree of stiffness to the hair. In contrast, the carboxylated polyurethane resin provides an elastic film on the hair. However, consumers equate a good hair spray with a degree of hair stiffness. The present hair styling mousse compositions, therefore, impart the desired stiffness to the hair, while further providing the benefits attributed to the carboxylated polyurethane resin, such as a low viscosity, an aqueous composition, reduced flaking, and good hair feel.

Nonlimiting examples of optional second hair fixative resins useful in the present hair spray compositions can be found in Grollier et al. U.S. Pat. No. 4,445,521, incorporated herein by reference. Specific second hair fixative resins include, but are not limited to, acrylamide copolymers, acrylamide/sodium acrylate copolymer, acrylate/ammonium methacrylate copolymer, acrylate copolymers, acrylic/acrylate copolymers, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, ammonium acrylate copolymers, ammonium vinyl acetate/acrylate copolymers, AMP acrylate/diacetoneacrylamide copolymers, AMPD acrylate/diacetoneacrylamide copolymers, butyl ester of ethylene/maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine copolymer, dodecanedioic acid/cetearyl alcohol/glycol copolymer, ethyl ester of PVM/MA copolymer, isopropyl ester of PVM/MA copolymer, karaya gum, methacryloyl ethyl betaine/methacrylate copolymers, octylacrylamide/acrylate/butylaminoethyl methacrylate copolymers, octylacrylamide/acrylate copolymers, phthalic anhydride/glycerin/glycidyl decanoate copolymer, phthalic/trimellitic/glycol copolymers, polyacrylamide, polyacrylamidomethylpropane sulfonic acid, polybutylene terephthalate, polyethylacrylate, polyethylene, polyquaternium-1, polyquaternium-2, poly quaternium-4, polyquaternium-5, polyquaternium-6, polyquaternium-7, polyquaternium-8, polyquaternium-9, polyquaternium-lo, polyquaternium-11, polyquaternium-12, polyquaternium-13, polyquaternium-14, polyquaternium-15, polyvinyl acetate, polyvinyl butyral, polyvinyl imidazolinium acetate, polyvinyl methyl ether, PVM/MA copolymer, PVP, PVP/dimethylaminoethylmethacrylate co-polymer, PVP/eicosene copolymer, PVP/ethyl methacrylate/methacrylic acid copolymer, PVP/hexadecene copolymer, PVP/VA copolymer, PVP/vinyl acetate/itaconic acid copolymer, shellac, sodium acrylate/vinyl alcohol copolymer, sodium carrageenan, starch diethylaminoethyl ether, stearylvinyl ether/maleic anhydride copolymer, sucrose benzoate/sucrose acetate isobutyrate/butyl benzyl phthalate copolymer, sucrose benzoate/sucrose acetate isobutyrate/butyl benzyl phthalate/methyl methacrylate copolymer, sucrose benzoate/sucrose acetate isobutyrate copolymer, vinyl acetate/crotonate copolymers, vinyl acetate/crotonic acid copolymer, vinyl acetate/crotonic acid/methacryloxybenzophenone-1 copolymer, vinyl acetate/crotonic acid/vinyl neo-decanoate copolymer, and mixtures thereof.

For hair styling mousse compositions, the kinematic viscosity of a solution of a polyurethane resin and an optional second hair fixative resin having a weight percent of total resin of 3% is less than about 1,000 centistokes (cs), i.e., about 1 to about 1,000 cs, preferably about 500 cs or less, more preferably about 100 cs or less, still more preferably less than about 50 cs, and most preferably less than about 40 cs.

In addition to the carboxylated polyurethane resin and the optional second hair fixative resin, the hair styling mousse compositions contain 0% to about 20%, by total weight of the composition, of a lower alcohol, i.e., an alcohol having one to seven carbon atoms. Preferably, the composition contains 0% to about 10%, by weight, of a lower alcohol. To achieve the full advantage of the present invention, the hair styling mousse composition is free of a lower alcohol. In order to reduce the adverse environmental affects attributed to volatile organic compounds, the amount of lower alcohol is maintained at as low a level as possible without adversely affecting the esthetics or efficacy of the hair styling mousse composition. Similarly, the amount of lower alcohol is kept at a minimum, and preferably the lower alcohol is absent from the mousse composition, such that the foaming ability of the carboxylated polyurethane resin is not adversely affected.

The lower alcohol typically used in the hair styling mousse composition is ethanol, although isopropyl alcohol also can be incorporated into the composition. The carboxylated polyurethane resins are readily solubilized in water and in a wide range of hydroalcoholic solutions, and in water without the addition of basic neutralizer, thereby permitting a decrease in the amount of or total elimination of, alcohol present in the hair styling mousse composition.

The hair styling mousse composition also contains about 70% to about 99%, by total weight of the composition, of water as a carrier. The amount of water is maximized in order to reduce the amount of VOC in the composition and to increase the foaming ability of the carboxylated polyurethane resin. Because the carboxylated polyurethane resins are hydrophilic, it is not necessary to include a base in the water to neutralize and solubilize the polyurethane resin. The carboxylated polyurethane resin also assists in solubilizing the optional second hair fixative resin, and in reducing the viscosity of the hair styling mousse composition.

Optional ingredients also can be incorporated into the hair styling mousse composition. The identity of the optional ingredients is not limited as long as the optional ingredients do not adversely affect the esthetics or efficacy of the hair styling mousse composition. For example, a hair styling mousse composition containing only a polyurethane resin, an optional second hair fixative resin, and water can be applied to the hair as a nonaerosol pump spray. By using a pump capable of introducing air into the pump spray, the mousse composition foams in a manner acceptable to consumers. The mousse composition can be modified for application as an aerosol spray by incorporating about 5% to about 30%, by weight of the composition, of a propellant. The carboxylated polyurethane resin and optional second hair fixative resin tolerate the propellant gases commonly used in aerosol compositions, such as the alkanes and carbon dioxide.

The optional propellant gas included in the hair styling mousse compositions can be any liquefiable gas conventionally used for aerosol products. Examples of compounds that are suitable for use as propellants are trichlorofluoromethane, dichlorodifluoromethane, dichlorotetrafluoroethane, monochlorodifluoromethane, trichlorotrifluoroethane, dimethyl ether, propane, n-butane, and isobutane, either singly or admixed. Water-soluble gases such as dimethyl ether, carbon dioxide, and/or nitrous oxide also can be used to obtain aerosol sprays having reduced flammability.

Water-immiscible, liquified, hydrocarbon and halogenated hydrocarbon gases such as propane, butane, and chlorofluorocarbons can be used advantageously to deliver the contents of an aerosol container without the dramatic pressure drops associated with other immiscible gases. The head space left inside the aerosol container is not a factor because the liquified gas sits on top of the aqueous composition and the pressure inside the container is maintained at the vapor pressure of the saturated hydrocarbon vapor.

Other insoluble, compressed gases such as nitrogen, helium, and fully fluorinated oxetanes and oxepanes also are useful to deliver the compositions from aerosol containers. If the propellant, such as dimethyl ether, incorporates a vapor pressure suppressant (e.g., trichloroethane or dichloromethane), the amount of suppressant is included as part of the propellant for weight percentage calculations.

The hair styling mousse compositions also can contain a variety of other nonessential, optional components. Such conventional optional ingredients are well known to those skilled in the art, e.g., emulsifiers or foaming agents, such as anionic or nonionic surfactants; preservatives, such as benzyl alcohol, methyl paraben, propyl paraben, or imidazolidinylurea; thickening agents, such as a gum or cellulose-based thickener; emollients, such as ethers or esters of fatty alcohols, or esters of fatty acids; nonionic conditioners, like silicones and hydrocarbons; cationic conditioners, such as cetyl trimethyl ammonium chloride, stearyl dimethyl benzyl ammonium chloride, and di(partially hydrogenated tallow) dimethyl ammonium chloride; coloring agents such as any of the FD&C or D&C dyes; perfume oils; and chelating agents such as ethylenediaminetetraacetic acid. These optional ingredients generally are included individually at a level of 0% to about 5%, by weight of the total composition.

The aqueous formulations of the present invention also can contain conventional hair treating adjuvants in amounts which generally range from 0% to about 2% by weight, and preferably 0% to about 1% by weight. Among the additives which can be used are plasticizers, such as glycols, phthalate esters, and glycerin; lubricants; and penetrants, such as various lanolin compounds, protein hydrolysates and other protein derivatives; ethylene adducts and polyoxyethylene cholesterol.

The hair styling mousse compositions of the present invention are prepared by simply admixing and dissolving the carboxylated polyurethane resin, the optional second hair fixative resin, and any optional ingredients into an aqueous or hydroalcoholic carrier. The resulting solution can be used in a pump spray, or can be pressurized by the addition of an aerosol propellant in accordance with methods well known in the art.

EXAMPLE A

Preparation of a Carboxylated Polyurethane Resin A

Polyoxyethylene diol having a number average molecular weight ($M_n$) of 8000 was heated under vacuum to 0.060% of water and 736 parts of the dried diol was added to 21 parts of diethylene glycol, 18 parts of dimethylolpropionic acid, and 2.84 parts of water. The mixture was heated with stirring until a homogeneous melt was obtained. Then, 139 parts of methylene bis-cyclohexyl-4-4'-diisocyanate were added. The NCO/OH ratio was 0.85. When the temperature reached about 64° C., 1.85 ml of dibutyltin dilaurate was added, and the mass was allowed to exotherm. The mass was heated at 100° C. for about one hour to complete formation of the polymer. The polyurethane resin had a weight average molecular weight ($M_w$) of 76,000 and dissolved in a slightly basic 55/45 ethanol/water solution (wt/wt) at a concentration of 5 wt. % to give a viscosity of 18 cps. The polyurethane resin had an acid value of 7.75 mg KOH/g resin, and a kinematic viscosity of 14.7 cs in 55/42/3 ethanol/water/polymer solution by weight. The polyurethane resin was applied to the hair as a hair styling aid, and imparted excellent properties to the hair, such as a crust rating of 8.3, a feel of 9.6, a flaking rating of 8.4, a set retention of 94% at 85% relative humidity (RH) after 30 minutes, and a set retention of 91% at 85% relative humidity (RH) after 60 minutes.

EXAMPLE B

Preparation of Polyurethane Resin B

Polyoxyethylene diol having an $M_n$ of 8000 was heated under vacuum to 0.215% of water, and 736 parts of the dried diol was added to 21 parts of diethylene glycol, 59 parts of dimethylolpropionic acid, and 1.81 parts of water. The mixture was heated with stirring until a homogeneous melt was obtained.

Then, 168 parts of methylene bis-cyclohexyl-4-4'-diisocyanate were added. NCO/OH ratio was 0.65. When the temperature reached about 70° C., 1.85 ml of dibutyltin dilaurate was added, and the mass was allowed to exotherm. The mass was heated at 100° C. for about one hour to complete formation of the polyurethane resin. The polyurethane resin had an $M_w$ of 15,000 and dissolved in slightly basic 55/45 ethanol/water (wt/wt) solution at a concentration of 5 wt. % was clear and had a viscosity of 10 cps. The polyurethane resin had an acid value of 24.22 g KOH/g resin, and a kinematic viscosity of 4.60 cps in 55/42/3 ethanol/water/polymer solution by weight. The polyurethane resin was used as a hair styling aid to impart a superior soft feel, excellent set retention, low crust, and low flaking properties to treated hair. Polyurethane Resin B imparted a crust rating of 4.5, a feel of 4.5, a flaking rating of 1.8, a set retention of 85% at 85% RH after 30 minutes to treated hair.

EXAMPLE C

Preparation of Polyurethane Resin C

Polyoxyethylene diol having an $M_n$ of 8000 was heated under vacuum to 0.060% of water, and 736 parts of the dried diol was added to 21 parts of diethylene glycol, 18 parts of dimethylolpropionic acid, and 0.96 part of water. The mixture was heated with stirring until a homogeneous melt was obtained. Then, 114 parts of methylene bis-cyclohexyl-4-4'-diisocyanate were added. The NCO/OH ratio was 0.85. When the temperature reached about 63° C., 1.85 ml of dibutyltin dilaurate was added, and the mass was allowed to exotherm. The mass was heated at 100° C. for about one hour to complete formation of the polyurethane resin. The polyurethane resin dissolved in slightly basic 55/45 ethanol/water solution (wt/wt) at a concentration of 5 wt. % was clear and had a viscosity of 14 cps. The polyurethane resin had an acid value of 8.01 mg KOH/g resin, and an $M_w$ of 40,000. The polyurethane resin was used as a hair styling aid to impart superior soft feel, excellent set retention, low crust, and low flaking properties to treated hair. Polyurethane Resin C imparted a crust rating of 4.9, a feel of 6.7, a flaking rating of 7, a set retention of 97% at 85% RH after 30 minutes, and a set retention of 95% at 85% RH after 60 minutes to treated hair.

EXAMPLE D

Preparation of Polyurethane Resin D

A batch of 13,147 parts of polyoxyethylene diol having an $M_n$ of 8000 was added to a five-gallon electrically heated reactor and heated under vacuum to dry the glycol. The dried diol was added to 368 parts of diethylene glycol and 321 parts of dimethylolpropionic acid, and the mixture was heated to 105° C. in order to melt the ingredients. The mixture was allowed to cool to about 175° F. to about 185° F. and the water level was analyzed by Karl Fisher method as 0.0675%. Then, 19.41 grams of water was added to the mixture to bring the total water to 28.75 grams of water.

A separate reactor contained 2073 parts of methylene bis(cyclohexyl-4-isocyanate). To the diols was added 33.04 cc of dibutyltin dilaurate. Then the isocyanate was heated to about 110°–115° F., and both liquids were forced out under nitrogen pressure using a piston cylinder at about a ratio of 0.1492. Twelve shots of liquid were pumped into a polypropylene tub and heated for one hour at 100° C. The NCO/OH ratio was 0.85.

The polyurethane resin was dissolved at 3 wt. % solids in 55/45 ethanol/water solution (wt/wt) and gave viscosities of 11 cps using a Brookfield viscometer. The polyurethane resin had a kinematic viscosity of 7.67 cps in 55/42/3 ethanol/water/polymer solution by weight. The polymer had an $M_w$ of 40,000, and was very similar to Polyurethane Resin C.

The polyurethane resin was used as a hair styling aid to give hair a superior soft feel, excellent set retention, low crust, and low flaking properties to treated hair.

EXAMPLE E

Preparation of Polyurethane Resin E

A batch of 13,147 parts of polyoxyethylene diol having an $M_n$ of 8000 was added to a five-gallon electrically heated reactor and heated under vacuum to dry the glycol. The dried diol was added to 368 parts of diethylene glycol and 321 parts of dimethylolpropionic acid, and the mixture was heated to 105° C. in order to melt the ingredients. The mixture was allowed to cool to about 175° F. to about 185° F. and a sample of the mixture was taken and analyzed for its water content by Karl Fisher method. The mixture had a water content of 0.0625% water and 26.66 grams of water was added to the mixture to bring the total water to 35.31 grams of water.

A separate reactor contained 2162 parts of methylene bis(cyclohexyl-4-isocyanate). To the diols was added 33.04 cc dibutyltin dilaurate. Then the diisocyanate was heated to about 110°–115° F., and both liquids were forced out under nitrogen pressure using a piston cylinder at about a ratio of 0.1555. Twelve shots of liquid were pumped into a polypropylene tub and heated for one hour at 100° C. The NCO/OH ratio was 0.85.

The polyurethane resin was dissolved at 3% solids in 55/45 ethanol/water solution (wt/wt) and gave a viscosity of 11.5 cps using a Brookfield viscometer. The polyurethane resin had a kinematic viscosity of 9.81 cs in 55/42/3 ethanol/ water/polymer solution by weight, and a molecular weight of 49,000. Polyurethane Resin E was similar to Polyurethane Resins C and D.

EXAMPLE F

Preparation of Polyurethane Resin F

Polyoxyethylene diol having an $M_n$ of 8000 was heated under vacuum to 0.060% of water, and 336 parts of the dried diol was added to 9.3 parts of diethylene glycol, 27 parts of dimethylolpropionic acid, 8.2 parts of diglycolamine and 0.002 part of water. The mixture was heated with stirring until a homogeneous melt was obtained. Then, 73 parts of methylene bis-cyclohexyl-4-4'-diisocyanate were added. The NCO/OH ratio was 0.65. When the temperature reached about 65° C., 0.92 ml of dibutyltin dilaurate was added, and the mass was allowed to exotherm. The mass was heated at 100° C. for about one hour to complete formation of the polymer. The polyurethane resin dissolved in slightly basic 55/45 ethanol/water solution (wt/wt) at a concentration of 5 wt. % was clear. The polyurethane resin had an $M_w$ of 26,000, and a kinematic viscosity of 5.93 cs in 55/42/3 ethanol/water/polymer solution by weight.

EXAMPLE G

Preparation of Polyurethane Resin G

Polyoxyethylene diol having an $M_n$ of 8000 was heated under vacuum to 0.061% of water, and 736 parts of the dried diol was added to 21 parts of diethylene glycol, 59 parts of dimethylolpropionic acid, and 1.11 part of water. The mixture was heated with stirring until a homogeneous melt was obtained. Then, 185 parts of methylene bis-cyclohexyl-4-4'-diisocyanate were added. The NCO/OH ratio was 0.85. When the temperature reached about 63° C., 1.85 ml of dibutyltin dilaurate was added, and the mass was allowed to exotherm. The mass was heated at 100° C. for about one hour to complete formation of the polymer.

The polyurethane resin had an $M_w$ of 21,000 and dissolved in slightly basic 55/45 ethanol/water solution (wt/wt) at a concentration of 5 wt. % was clear and had a viscosity of 10 cps. The polyurethane resin had a kinematic viscosity of 6.15 cps in 55/42/3 ethanol/water/polymer solution by weight. The polyurethane resin was used as a hair styling aid, and imparted a crust rating of 6.3, a feel of 8.1, a flaking rating of 8.3, a set retention of 81% at 85% RH after 30 minutes, and a set retention of 68% at 85% RH after 60 minutes to treated hair.

EXAMPLE H

Preparation of Polyurethane Resin H

Polyoxyethylene diol having an $M_n$ of 8000 as heated under vacuum to 0.156% of water and 756 parts of the dried diol was added to 21 parts of diethylene glycol, 39 parts of dimethylolpropionic acid, and 0.25 part of water. The mixture was heated with stirring until a homogeneous melt was obtained. Then, 136 parts of methylene bis-cyclohexyl-4-4'-diisocyanate were added. The NCO/OH ratio was 0.75. When the temperature reached about 66° C., 1.85 ml of dibutyltin dilaurate was added, and the mass was allowed to exotherm. The mass was heated at 100° C. for about one hour to complete formation of the polymer. The polyurethane resin ($M_w$ of 24,000) dissolved in a slightly basic 55/45 ethanol/water solution (wt/wt) at a concentration of 5 wt. % to produce a clear solution with a viscosity of 11 cps.

Polyurethane Resin H was used as a hair styling aid. The polyurethane resin imparted a crust rating of 6.9, a feel of 5.5, a set retention of 95% at 85% RH after 30 minutes, and a set retention of 90% at 85% RH after 60 minutes to treated hair.

EXAMPLE I

Preparation of Polyurethane Resin I

Polyoxyethylene diol having an $M_n$ of 8000 was heated under vacuum to 0.032% of water and 736 of the dried diol was added to 21 parts of diethylene glycol, 18 parts of dimethylolpropionic acid, and 2.06 parts of water. The mixture was heated with stirring until a homogeneous melt was obtained. Then, 113 parts of methylene bis-cyclohexyl-4-4'-diisocyanate were added. The NCO/OH ratio was 0.75. When the temperature reached about 65° C., 1.85 ml of dibutyltin dilaurate was added, and the mass was allowed to exotherm. The mass was heated at 100° C. for about one hour to complete formation of the polymer. The polyurethane resin dissolved in a slightly basic 55/45 ethanol/water solution (wt/wt) at a concentration of 5 wt. % to produce a clear solution with a viscosity of 13 cps. The polyurethane resin ($M_w$ of 35,000) had a kinematic viscosity of 6.50 cs in 55/42/3 ethanol/water/polymer by weight solution. Polyurethane Resin I was used as a hair styling aid. The polyurethane resin imparted a crust rating of 4.2, a feel of 4.8, a flaking rating of 4.2, a set retention of 86% at 85% RH after 30 minutes, and a set retention of 73% at 85% RH after 60 minutes to treated hair.

EXAMPLE J

Preparation of Polyurethane Resin J

A polyoxyethylene diol having an $M_n$ of 8000 was heated under vacuum to 0.048% of water, then 744 parts of the dried diol was added to 21 parts diethylene glycol, 4.3 parts dimethylolpropionic acid, and 0.37 parts water. The resulting mixture was heated, with stirring, until a homogenous melt was obtained.

Then, 88 parts methylene bis-cyclohexyl-4-4'-diisocyanate was added to the mixture. The NCO/OH ratio was about 0.98. When the temperature reached about 65° C., 2.25 ml of dibutyl tin dilaurate was added to the mixture, and the mass exothermed. The mass then was heated to 100° C., and held at 100° C. for about one hour to complete polyurethane formation. The polyurethane resin had an $M_w$ of 141,000. At 5% concentration, the polyurethane resin dissolved in 55/45 ethanol water to give a solution having a viscosity of 180 cps. At a concentration of 3%, in 60/40 propylene glycol/water, the solution had a viscosity of 5300 cps.

EXAMPLE K

Preparation of Polyurethane Resin K

A polyoxyethylene diol having an $M_n$ of 8000 was heated under vacuum to 0.037% of water, then 744 parts of the dried diol was added to 21 parts diethylene glycol, 18.6 parts dimethylolpropionic acid, and 0.23 parts water. The resulting mixture was heated, with stirring, until a homogenous melt was obtained. Then, 115 parts methylene bis-cyclohexyl-4-4'-diisocyanate was added to the mixture. The NCO/OH ratio was about 0.98. When the temperature reached about 65° C., 2.25 ml dibutyl tin dilaurate was added to the mixture, and the mass exothermed. The mass then was heated to 100° C., and held at 100° C. for about one hour to complete polyurethane formation. The polyurethane resin had an $M_w$ of 63,000. At 5% concentration, the polyurethane resin dissolved in 55/45 ethanol water to give a solution having a viscosity of 1680 cps, and a reduced viscosity of 225 cps upon the addition of 2 ml ammonia to 180 grams of the solution. At a concentration of 3%, in 60/40 propylene glycol/water, the solution had a viscosity of 144 cps.

EXAMPLE L

Preparation of Polyurethane Resin L

A polyoxyethylene diol having an $M_n$ of 8000 was heated under vacuum to 0.062% of water, then 470 parts of the dried diol was added to 13.2 parts diethylene glycol, 11.4 parts dimethylol propionic acid, and 0.55 parts water. The resulting mixture was heated, with stirring, until a homogenous melt was obtained. Then, 76 parts methylene bis-cyclohexyl-4-4'-diisocyanate was added to the mixture. The NCO/OH ratio was about 0.90. When the temperature reached about 61° C., 1.44 ml dibutyl tin dilaurate was added to the mixture, and the mass exothermed. The mass was heated to 100° C., and held at 100° C., for about one hour to complete formation of the polyurethane. The polyurethane resin had an M, of 46,000. At a 5% concentration, the polyurethane dissolved in 55/45 ethanol water to give a solution having a viscosity of 13 cps, and a reduced viscosity of 12 cps upon the addition of 2 ml ammonia to 180 grams of the solution. At a concentration of 3%, in 60/40 propylene glycol/water, the solution had a viscosity of 64 cps. At a concentration of 5%, in 30/70 ethanol/water, the solution had a viscosity of 34 cps, and upon neutralization, the viscosity dropped to 16 cps.

EXAMPLE M

Preparation of Polyurethane Resin M

Polyoxyethylene diol having an $M_n$ of 8000 was heated under vacuum to 0.053% of water, and 473 parts of the dried diol was added to 13.2 parts of diethylene glycol, 11.5 parts of dimethylolpropionic acid, and 0.12 part of water. The mixture was heated with stirring until a homogeneous melt was obtained. Then, 69.7 parts of methylene bis-cyclohexyl-4-4'-diisocyanate were added during which the temperature decreased. The NCO/OH ratio was 0.90. When the temperature reached about 64° C., 0.75 ml of dibutyltin dilaurate was added. The mass was held at 100° C. for about one hour.

At 5 wt. % concentration, the polyurethane resin dissolved in 55/45 ethanol/water (wt/wt) solution to give a milky solution having a viscosity of 12 cps. At 5% concentration in 30/65 ethanol/water (wt/wt), the viscosity was 34 cps. Upon addition of dilute ammonia, the viscosity of the former solution was 13 cps, and the viscosity of the latter solution was 16 cps.

EXAMPLE N

Preparation of Polyurethane Resin N

Polyoxyethylene diol having an $M_n$ of 8000 was heated under vacuum to 0.050% of water, and 474 parts of the dried diol was added to 13 parts of diethylene glycol, 12 parts of dimethylolpropionic acid, and 0.15 part of water. The mixture was heated with stirring until a homogeneous melt was obtained. Then, 73 parts of methylene bis-cyclohexyl-4-4'-diisocyanate were added. The NCO/OH ratio was 0.94.

When the temperature reached about 61° C., 1.5 ml of dibutyltin dilaurate was added. The mass was heated at 100° C. for about one hour.

The polyurethane resin was dissolved at 5 wt. % concentration in 55/45 and 30/65 ethanol/water (wt/wt), giving viscosities of 12.0 and 23.5 cps, respectively. When the pH was raised with dilute ammonia, the viscosities were 9 and 14.4 cps, respectively.

EXAMPLE O

Preparation of Polyurethane Resin O

Polyoxyethylene diol having an $M_n$ of 8000 was heated under vacuum to 0.208% of water, and 744 parts of the dried diol was added to 21 parts of diethylene glycol, 19 parts of dimethylolpropionic acid, and 2.90 part of water. The mixture was heated until a homogeneous melt was obtained. Then, 106 parts of methylene bis-cyclohexyl-4-4'-diisocyanate were added. The NCO/OH ratio was 0.50. When the temperature was about 63° C., 2.25 ml of dibutyltin dilaurate was added. The mass was allowed to exotherm, and then heated at 100IC for 1.5 hours. At a concentration of 5 wt. % in 55/45 ethanol/water (wt/wt), the polyurethane resin produced a milky solution having a viscosity of 12.5 cps, and at 5 wt. % in 30/60 ethanol/water (wt/wt), the milky solution had a viscosity of 15.0 cps. Both solutions became clear upon the addition of dilute ammonia, with viscosities of 14 and 13 cps, and solutions of 2 wt. % and 2.5 wt. % polyurethane in water had viscosities of 4.5 and 7.0 cps, respectively.

EXAMPLE P

Preparation of Polyurethane Resin P

Polyoxyethylene diol having an $M_n$ of 8000 was heated under vacuum to 0.271% of water, and 736 parts of the dried diol was added to 21 parts of diethylene glycol, 38 parts of dimethylolpropionic acid, and 0.271 part of water. The mixture was heated with stirring until a homogeneous melt was obtained. Then, 145 parts of methylene bis-cyclohexyl-4-4'-diisocyanate were added. The NCO/OH ratio was 0.75. When the temperature reached about 59° C., 1.85 ml of dibutyltin dilaurate was added, and the mass was allowed to exotherm. The mass was heated at 100° C. for about one hour to complete formation of the polymer. At a concentration of 5 wt. %, the polyurethane resin formed a milky solution in 55/45 ethanol/water (wt/wt) having a viscosity of 9.0 cps. The mixture was made basic with dilute ammonia to provide a water clear solution having a viscosity of 15.3 cps.

EXAMPLE Q

Preparation of Polyurethane Resin Q

Polyoxyethylene diol having an $M_n$ of 8000 was heated under vacuum to 0.276% of water, and 736 parts of the dried diol was added to 21 parts of diethylene glycol, 24 parts of dimethylolpropionic acid, and 0.270 part of water. The mixture was heated with stirring until a homogeneous melt was obtained. Then, 124 parts of methylene bis-cyclohexyl-4-4'-diisocyanate were added. The NCO/OH ratio was 0.75. When the temperature reached about 56° C., 1.85 ml of dibutyltin dilaurate was added, and the mass was allowed to exotherm. The mass was heated at 100° C. for about one hour to complete formation of the polymer. The polyurethane resin formed a milky solution in 55/45 ethanol/water (wt/wt) at a concentration of 5 wt. %. The pH was 5.0 and the viscosity was 9.0 cps. The pH of about 20 cc of solution was increased to about 7 with dilute ammonia, potassium-hydroxide, sodium bicarbonate, and lithium acetate dihydrate. The slightly basic solutions were water clear, and the viscosity of solution with ammonia was 15 cps.

EXAMPLE R

Preparation of Polyurethane Resin R

Polyoxyethylene diol having an $M_n$ of 1450 (C1400) was heated under vacuum to a water level of 0.244% and the 227 parts of the dried diol was added to 156 parts of polyoxyethylene diol having an $M_n$ of 1000, 94 parts of polyoxyethylene diol having an mn of 600 (C600), 62 parts of polyoxyethylene diol having an $M_n$ of 400 (C400), 120 parts of ethylene glycol, 381 parts of polyoxytetramethylene glycol having an $M_n$ of 2000 (TR2000), 104 parts of polyoxypropylene glycol having an average molecular weight of 1025 (C1025), 93 parts of dimethylolpropionic acid, and 4.51 parts of water. The mixture was heated with stirring until a homogeneous melt was obtained. Then, 1026 parts of methylene bis-cyclohexyl-4-4 '-diisocyanate were added. The NCO/OH ratio was 0.98. When the temperature reached about 50° C., 3.4 ml of stannous octoate ($T_g$) was added, and the mass was allowed to exotherm. The mass was heated at 100° C. for about one hour to complete formation of the polymer. The polyurethane resin had a tear strength of 520 pounds per inch, and modulus at 100% elongation of 1470 pounds per square inch compared to values of 260 pounds/inch and 670 pounds per square inch for a similar polyurethane resin made without dimethylolpropionic acid. The polyurethane resin had a water content of 21% and a linear expansion of 8% after exposure to water and similar polyurethane resin without any dimethylolpropionic acid had corresponding values of 25% and 11%. The polyurethane resin was dissolved in 75/25 tetrahydrofuran/ethanol to give a viscosity of 15 cps. Upon the addition of 5 wt. % water, the viscosity increased to 6120 cps.

EXAMPLE S

Preparation of Polyurethane Resin S

Polyoxyethylene diol having an $M_n$ of 8000 was heated under vacuum to 0.099% of water and 306 parts of the dried diol was added to 34 parts of a block copolymer of ethylene oxide and propylene oxide made by BASF under the tradename of F127, 9.5 parts of diethylene glycol, 27 parts of dimethylolpropionic acid, and 1.30 parts of water. The mixture was heated with stirring until a homogeneous melt was obtained. Then, 77 parts of methylene bis-cyclohexyl-4-4'-diisocyanate were added. The NCO/OH ratio was 0.65. When the temperature reached about 67° C., 0.68 ml of dibutyltin dilaurate was added, and the mass was allowed to exotherm. The mass was heated at 100° C. for about one hour to complete formation of the polyurethane resin. The polyurethane resin can be dissolved in slightly basic 55/45 ethanol/water (wt/wt) at a concentration of 5 wt. % to produce a clear solution with a viscosity of less than 20 cps.

EXAMPLE T

Preparation of Polyurethane Resin T

Polyoxyethylene diol having an $M_n$ of 8000 was heated under vacuum to 0.072% of water, and 343 parts of the dried diol was added to 18 parts of polyoxypropylene glycol of 425 molecular weight, 10 parts of diethylene glycol, 18 parts of dimethylolpropionic acid, and 0.43 part of water. The mixture was heated with stirring until a homogeneous melt was obtained. Then, 79 parts of methylene bis-cyclohexyl-4-4'-diisocyanate were added. The NCO/OH ratio was 0.85. When the temperature reached about 58° C., 0.68 ml of dibutyltin dilaurate was added, and the mass was allowed to exotherm. The mass was heated at 100IC for about one hour to complete formation of the polymer. The polyurethane resin dissolved in 55/45 ethanol/water (wt/wt) at a concentration of 5 wt. % to produce a clear solution with a viscosity of 12 cps. The polyurethane resin can be blended with low set retention polymers to improve set retention without significantly affecting sprayability.

EXAMPLE U

Preparation of Polyurethane Resin U

Polyoxyethylene diol having an $M_n$ of 8000 and polyoxyethylene diol having an $M_n$ of 1450 were heated under vacuum to 0.132% of water, and 291 parts of the higher molecular weight dried diol and 15.3 parts of lower molecular weight dried diol were added to 9.5 parts of dipropylene glycol, 27 parts of dimethylolpropionic acid, 34 parts of polyoxypropylene glycol of 425 molecular weight, and 1.146 part of water. The mixture was heated with stirring until a homogeneous melt was obtained. Then, 89 parts of methylene bis-cyclohexyl-4-4'-diisocyanate were added. The NCO/OH ratio was 0.65. When the temperature reached about 67° C., 0.68 ml of dibutyltin dilaurate was added, and the mass was allowed to exotherm. The mass was heated at 100° C. for about one hour to complete formation of the polymer. The polyurethane resin dissolved in slightly basic 55/45 ethanol/water (wt/wt) at a concentration of 5 wt. % was clear, and had a viscosity of 8 cps. The polyurethane resin was used in a hair styling aid to give treated hair a superior soft feel, excellent set retention, low crust, and low flaking properties.

EXAMPLE V

Preparation of Polyurethane Resin V

Polyoxyethylene diol having an $M_n$ of 8000 was heated under vacuum to 0.028% of water, and 736 parts of the dried diol was added to 21 parts of cyclohexanedimethanol, 18 parts of dimethylolpropionic acid, and 1.21 parts of water. The mixture was heated with stirring until a homogeneous melt was obtained. Then, 102 parts of methylene bis-cyclohexyl-4-4'-diisocyanate were added. The NCO/OH ratio was 0.85. When the temperature reached about 65° C., 1.85 ml of dibutyltin dilaurate was added, and the mass was allowed to exotherm. The mass was heated at 100° C. for about one hour to complete formation of the polyurethane resin. The polyurethane resin can be dissolved in slightly basic 55/45 ethanol/water solution (wt/wt) at a concentration of 5 wt. % to give a low viscosity clear solution. The polyurethane resin was used as a hair styling aid to give treated hair a superior soft feel, excellent set retention, low crust, and low flaking properties.

To demonstrate the hair styling mousse compositions of the present invention, several aerosol compositions containing about 10% VOC (i.e., VOC is the sum of lower alcohol and propellant in the mousse composition) were prepared. Each composition contained 10% by weight of a propellant blend containing 70% hydrofluorocarbon 152a and 30% butane by volume. The mousse compositions were free of a lower alcohol. In some mousse compositions, the carboxylated polyurethane resin was the sole hair styling aid. In other compositions, an optional second hair fixative resin was present in addition to the carboxylated polyurethane resin. The compositions are summarized below as Examples 1–8 in Tables 1 and 2.

TABLE 1

| Example | 1 | 2 | 3 | 4 | 5 |
|---|---|---|---|---|---|
| Ingredients: | | | | | |
| Deionized water | 87.48[1] | 87.80 | 87.30 | 87.62 | 87.80 |
| Polyurethane Resin A[2] | 1.00 | 1.00 | 1.00 | 1.00 | — |
| Polyurethane Resin C[3] | — | — | — | — | 1.00 |
| AMP[4] | 0.10 | 0.10 | 0.28 | 0.28 | 0.10 |
| CELQUAT L200[5] | 1.00 | 1.00 | — | — | 1.00 |
| AMPHOMER[6] | — | — | 1.00 | 1.00 | — |
| TAURANOL 78[7] | 0.20 | — | 0.20 | — | — |
| Lauramide DEA | 0.02 | — | 0.02 | — | — |
| Isosteareth 10 | 0.10 | — | 0.10 | — | — |
| Fragrance | 0.10 | 0.10 | 0.10 | 0.10 | 0.10 |
| Propellant Blend[8] | 10.00 | 10.00 | 10.00 | 10.00 | 10.00 |
| Foam | Very creamy | Creamy | Very creamy | Creamy | Less creamy |
| Foam Breaking | Very slow | Slow | Fast | Very fast | |

[1]expressed as % by weight of the composition;
[2]the carboxylated polyurethane resin of Example A;
[3]the carboxylated polyurethane resin of Example C;
[4]2-amino-2-methylpropanol, available from Angus Chemical Co., Northbrook, IL;
[5]polyquaternium-4, a copolymer of hydroxyethylcellulose and diallyldimethyl ammonium chloride, available from National Starch and Chemical Corp., Bridgewater, NJ;
[6]octylacrylamide/acrylates/butylaminoethyl methacrylate copolymer, available from National Starch and Chemical Corp.;
[7]sodium cocoyl isethionate, available from Finetex, Inc., Elmwood Park, NJ; and
[8]butane (30% by volume) and hydrofluorocarbon 152a (70% by volume).

The hair styling mousse compositions of Examples 1-5 were prepared by warming the deionized water to about 60° C. Then, with agitation, the carboxylated polyurethane resin and the AMP were added to the warm water. When the mixture was homogeneous, the mixture was cooled to room temperature, followed by the addition of CELQUAT L200 or AMPHOMER. The resulting mixture was stirred until homogeneous, then the remaining ingredients were added with stirring. The resulting solution was added to a container, which was crimped, and then charged with the propellant blend.

The data summarized in Table 1 shows that a present mousse composition generates a consumer-acceptable foam, even when the mousse composition is free of a foaming surfactant, i.e., Examples 2, 4, and 5. The presence of a foaming surfactant in Examples 1 and 3 merely provides a creamier foam. The amount of foam and the foam quality of mousse compositions containing a foaming surfactant and mousse compositions free of a foaming surfactant are comparable.

Table 1 also illustrates that a carboxylated urethane resin can be used in conjunction with an optional second hair fixative resin to provide a useful hair styling mousse composition. In particular, the mousse compositions of Examples 1, 2, and 5 incorporate a cationic second hair fixative resin (i.e., CELQUAT L200), and the compositions of Examples 3 and 4 incorporate an anionic second hair fixative resin (i.e., AMPHOMER).

The presence of an optional second hair fixative resin did not adversely affect the ability of the carboxylated polyurethane resin to generate a foam, even in the absence of a foaming surfactant. Table 1 further shows that foam breaking properties can be adjusted from very slow to very fast, depending on the carboxylated polyurethane resin, the optional second hair fixative resin, and the amount of AMP present in the mousse composition, and on the presence of foaming surfactants in the hair styling mousse composition.

Table 2 summarizes the hair styling mousse compositions of Examples 6–8, which were prepared using a commercial carboxylated polyurethane resin. The mousse compositions of Examples 6–8 were prepared in an essentially identical manner as the compositions of Examples 1–5. The carboxylated polyurethane resin used in Examples 6–8 is a copolymer of polyvinylpyrrolidone and a polyurethane, showing that that carboxyl group of the carboxylated polyurethane resin can be a carboxylic acid group or an ester group.

TABLE 2

| Example/Ingredients | 6 | 7 | 8 |
|---|---|---|---|
| Deionized Water | 73.07[1] | 58.10 | 74.91 |
| PECOGEL H-12[9] | 14.97 | 30.01 | 14.95 |
| BRIJ-30[10] | 1.80 | — | — |
| BRIJ-700[11] | — | 1.76 | — |
| Mineral Oil | 0.14 | 0.13 | 0.14 |
| A-31 Propellant[12] | 10.02 | 10.00 | 10.00 |
| Foam Density (g/cc) | 0.0310 | 0.0468 | 0.0470 |
| Viscosity (cp) | 28 | 40 | 26 |
| pH | 7.90 | 7.81 | 7.00 |
| Foam Quality | Creamy, rich, breaks slowly | Stiff foam, grows, breaks slowly | Creamy, rich, crackling, breaks quickly |
| Dry Film Quality | Cloudy, waxy, soft | Grainy, waxy, soft | Clear, hard |
| Hir Set Retention, (1 hr., 85% RH) | Poor | Poor | Better than control |

[9]PECOGEL H-12 is a 12% wt. ester polyurethane, available from Phoenix Chemicals Inc., Somerville, NJ;
[10]Laureth-4, available from ICI Americas, Inc., Wilmington, DE;
[11]Steareth-100, available from ICI Americas, Inc., Wilmington, DE; and
[12]isobutane.

The data summarized in Table 2 shows that a hair styling mousse composition having consumer-acceptable foam quantity and quality can be provided by a carboxylated polyurethane resin having ester carboxyl groups, even when a foaming surfactant is excluded from the composition (i.e., Example 8) and a defoaming component (i.e., mineral oil) is present in the composition. The mousse compositions also had a low viscosity making application to the hair by rubbing with the fingertips easy and efficient.

Table 2 also illustrates that preferred embodiments of the present invention do not incorporate a foaming surfactant into the hair styling mousse composition. In particular, Example 8 shows that a mousse composition containing a carboxylated polyurethane resin and free of a foaming surfactant, produces a foam density (0.047 g/cc) and foam quality comparable to FINESSE MOUSSE, a commercial product available from Helene Curtis, Inc., Chicago, Ill., and having a foam density of 0.045 g/cc. The mousse composition of Example 8 generates a foam that is equal in amount, and better in quality, than the foam generated by the mousse composition of Example 7, which incorporates a foaming surfactant. In preferred embodiments, a hair styling mousse composition of the present invention is free of a lower alcohol, and generates a foam density of at least 0.047 g/cc, i.e., 0.047 to about 0.06 g/cc.

The compositions of Examples 6 and 7, which incorporate a foaming surfactant, also provided a waxy, soft film on the hair that failed to provide good hair set retention. In contrast, the composition of Example 8, which is free of a foaming surfactant, provided a clear hard film on the hair. The mousse composition of Example 8 not only provided a better dry film quality than the mousse compositions of Examples 6 and 7, but also provided a hair set retention comparable to a control mousse composition containing AMPHOMER as the hair fixative resin. The hair set retention provided by the mousse composition of Example 8 is improved because Example 8 is free of surfactants. Surfactants plasticize dry resinous films left on the hair, which adversely affects the hair retention properties of the resin. Accordingly, it was observed that a foaming surfactant can impede the ability of the carboxylated polyurethane resin to provide a protective film on the hair, and, therefore, can adversely affect hair set retention because the highly hydrophilic nature of the foaming surfactants attracts water, plasticizes the resin, and helps destroy the hair set.

Examples 1–8 in Tables 1 and 2 further show that hair styling mousse compositions containing a carboxylated polyurethane resin and an optional second hair fixative resin, and having a low VOC (i.e., 10% by weight propellant and free of a lower alcohol) and a low viscosity, can be prepared. The second hair fixative resin is sufficiently solubilized, or dispersed, in the water, and, after the foam is broken, the hair styling mousse composition has a sufficiently low viscosity for easy and uniform application to the hair.

Experiments also were performed which duplicate air drying of a hair styling mousse composition after application to the hair. It was found that a carboxylated polyurethane resin, or a mousse composition of the present invention, gels within one hour after application to the hair. In contrast, a composition containing only AMPHOMER, i.e., a standard hair fixative resin in the art and used as a control, did not gel after air drying for two hours. Furthermore, hair treated with a hair styling mousse composition had a soft, natural feel and appearance, without excessive flaking or crust. In particular, the hair crust test measures the hardness and/or stiffness of hair treated with a hair styling mousse composition. Hair styling mousse compositions that provide natural, or reduced, crusts are desired. The hair flaking test measures the amount of flakes or dust that form on the hair after combing hair that has been treated with the mousse composition and dried.

In addition, hair set retention tests were performed. Set retention tests measure the ability of a hair styling mousse composition to hold or retain a hair style for an extended time at a particular relative humidity. Set retention is measured by applying 0.5 cc (cubic centimeter) of the hair styling mousse composition to a one gram hair tress, and testing six or more tresses per composition. The sprayed tresses were allowed to dry overnight, at 30% relative humidity, in a zigzag shape. The tresses were hung inside a humidity chamber at 25° C. and a predetermined relative humidity (i.e., 85% RH). The relaxed length was recorded of the tresses and set retention was calculated using the equation:

$$\% \text{ Set Retention} = \frac{L - L_t}{L - L_o} \times 100,$$

wherein L is the length of the fully extended tress, $L_o$ is the length of sprayed hair before relaxation, $L_t$ is the length after exposure for a time, t.

The hair set retention results were compared to the results provided by a negative control containing only water. The comparative test shows that hair styling mousse compositions containing a carboxylated polyurethane resin and a second hair fixative resin (i.e., GANTREZ A425, a partial butyl ester of a copolymer of vinyl methyl ether and maleic anhydride, available commercially from ISP, Wayne, N.J.) performed essentially as well as a hair spray composition containing only AMPHOMER. Such results are good because AMPHOMER is the hair fixative resin used in successful commercial hair styling mousse compositions.

Another important property of a present hair styling mousse composition is the ability to wash the hair setting resins from the hair, and thereby avoid polymer build-up on the hair. In accordance with an important feature of the present invention, the carboxylated polyurethane resin and the second hair fixative resin used in the hair styling mousse composition can be removed from the hair by simply shampooing the hair. The unexpected washability of the hair styling mousse composition is attributed to the acid value of the carboxylated polyurethane resin. When the acid value of the polyurethane resin is at least about 7 mg KOH/g of resin, the polyurethane resin can be rinsed from the hair during shampooing without the need to neutralize the resin with an organic base.

The acid value is an indication of the number pendant carboxylic acid groups on the polyurethane resin backbone. Although noncarboxylated polyurethane resins are hydrophilic, they are difficult to wash from the hair in a short time. Washability is enhanced by incorporating pendant carboxylic acid groups onto the polyurethane backbone.

The effect of acid value is illustrated by Polyurethane Resins B and C, which show that washability is independent of $M_w$ or R-value, but requires a carboxylated polyurethane resin having an acid value of about 7 mg KOH/g of resin or greater, e.g., about 7 to about 50 mg KOH/g resin. In particular, Polyurethane Resin A has an R-value of 0.88, an $M_w$ of about 76,000, and an acid value of 7.75. Polyurethane Resin B has an R-value of 0.65, an $M_w$ of about 15,000, and an acid value of 24.22. Polyurethane Resin C has an R-value of 0.85, an $M_w$ of about 40,000, and an acid value of 8.01. Polyurethane Resins A, B, and C each are washable from hair because each has an acid value of at least 7 mg KOH/g of resin.

The acid value was measured by titrating a solution of the resin with potassium hydroxide. The acid value is expressed in milligrams of KOH per gram of carboxylated polyurethane resin. The washability of the resin was determined by applying 3 wt. % solution of polyurethane resin onto clean, 2 gram, 6-inch long hair tresses, allowing the hair to dry, then washing the hair tresses with shampoo and warm water for about 3 minutes.

Many modifications and variations of the invention as hereinbefore set forth can be made without departing from the spirit and scope thereof, and, therefore, only such limitations should be imposed as are indicated by the appended claims.

What is claimed is:

1. A hair styling mousse composition consisting of:
   (a) about 0.25% to about 6% by weight of a carboxylated polyurethane resin;
   (b) about 0% to about 6% by weight of a second hair fixative resin;
   (c) about 0% to about 20% by weight of a lower alcohol; and
   (d) about 70% to about 90% by weight water;
   wherein the carboxylated polyurethane resin has a weight average molecular weight of about 10,000 to about 150,000, a polydispersibility index of about 1 to about 4, an acid value of about 7 mg. to about 50 mg. KOH per g. resin, a melting point of about 40° C. to about 120° C. and is a reaction product of a mixture consisting of:
   (a) a diol component comprising a polyoxyalkylene diol;
   (b) an alkylene glycol;
   (c) a diisocyanate;
   (d) water in an amount of about 0.05% to about 0.5% by weight of the mixture; and
   (e) a 2,2-di(hydroxymethyl) alkanoic acid,
   wherein the ratio of isocyanate groups to hydroxyl groups in the water, diol, and glycol is about 0.5 to about 1.

* * * * *